United States Patent
Balceta et al.

[11] Patent Number: 6,068,621
[45] Date of Patent: May 30, 2000

[54] ARTICULATING CANNULA

[75] Inventors: Jobert Balceta, San Jose; Peter Thornton, Los Altos, both of Calif.

[73] Assignee: Embol X, Inc., Mountain View, Calif.

[21] Appl. No.: 09/196,942

[22] Filed: Nov. 20, 1998

[51] Int. Cl.[7] ................................................. A61M 31/00
[52] U.S. Cl. ............................... 604/500; 604/95; 604/96
[58] Field of Search ................................... 604/164, 165, 604/48, 500, 507, 508, 509, 510, 93, 96, 103, 264, 523, 528, 526, 524, 95, 104, 105, 106, 107, 108, 109; 600/433, 434, 435; 606/198, 200, 108

[56] References Cited

U.S. PATENT DOCUMENTS

| | | |
|---|---|---|
| 3,896,816 | 7/1975 | Mattler . |
| 4,522,195 | 6/1985 | Schiff ........................................ 604/96 |
| 4,719,924 | 1/1988 | Crittenden et al. ...................... 604/528 |
| 4,886,067 | 12/1989 | Palermo ................................. 604/164 |
| 4,893,810 | 1/1990 | Lee . |
| 4,898,577 | 2/1990 | Badger et al. ........................... 604/528 |
| 4,917,102 | 4/1990 | Miller et al. ............................. 604/164 |
| 5,030,204 | 7/1991 | Badger et al. . |
| 5,312,344 | 5/1994 | Grinfeld et al. . |
| 5,425,708 | 6/1995 | Nasu . |
| 5,487,757 | 1/1996 | Truckai et al. ............................ 604/95 |
| 5,520,222 | 5/1996 | Chikama ................................. 604/524 |
| 5,527,279 | 6/1996 | Imran ........................................ 604/95 |
| 5,531,677 | 7/1996 | Lundquist et al. ........................ 604/22 |
| 5,632,734 | 5/1997 | Galel et al. ............................. 604/524 |
| 5,682,906 | 11/1997 | Sterman et al. ........................ 604/500 |
| 5,695,519 | 12/1997 | Summers et al. ....................... 606/200 |
| 5,700,269 | 12/1997 | Pinchuk et al. ......................... 606/108 |
| 5,769,816 | 6/1998 | Barbut et al. ............................. 604/96 |
| 5,776,115 | 7/1998 | Antoshkiw et al. .................... 604/524 |
| 5,792,094 | 8/1998 | Stevens et al. ........................... 604/96 |
| 5,800,457 | 9/1998 | Gelbfish ................................. 606/200 |
| 5,846,260 | 12/1998 | Maahs ................................... 606/200 |
| 5,853,400 | 12/1998 | Samson ................................. 604/528 |
| 5,865,802 | 2/1999 | Yoon et al. ............................... 604/96 |

*Primary Examiner*—Ronald Stright
*Assistant Examiner*—Jeremy Thissell
*Attorney, Agent, or Firm*—Lyon & Lyon LLP

[57] ABSTRACT

A cannula possessing a distal region and a proximal region, a slider mounted on the cannula, and a manipulator wire connecting the distal region and the slider, is articulated by proximal and distal displacements of the slider with respect to the distal end of the cannula.

5 Claims, 7 Drawing Sheets

ARTICULATING CANNULA

INTRODUCTION

This invention relates to medical devices, and more particularly relates to an articulating cannula for use in cardiopulmonary bypass surgery, heart surgery, and other medical procedures.

BACKGROUND OF THE INVENTION

During heart surgery and other operations, surgeons often clamp major vessels to occlude blood flow within the vessels. Because such clamping may cause trauma to the blood vessel, catheters with occluding balloons have been developed. For example, Nasu, U.S. Pat. No. 5,425,708, discloses a catheter or cannula with an L-shaped distal region. About the end of the distal region is positioned a vessel-occluding balloon. Such a device requires an insertion point adjacent to where the distal end of the catheter will be located. Alternatively, rather than use the L-shaped device as disclosed by Nasu, a surgeon could insert a flexible cannula such as disclosed by Grinfeld et al., U.S. Pat. No. 5,312,344, into, for example, the femoral artery and guide the distal end to where therapy is desired. If necessary, balloons at the distal end are then inflated.

However, both methods of therapy have certain drawbacks. For instance, an L-shaped catheter is not easily inserted into a vessel because the distal end is at right angles to the main shaft of the catheter. Thus, a surgeon must make an incision of a size adequate to accommodate the necessary maneuvering before insertion into the vessel. Instead, if a flexible cannula is inserted from the ascending aorta or femoral artery, the surgeon must contend with the difficulties and dangers of remotely guiding the distal end into its desired location. Therefore, there is a need in the art for an articulating cannula which can be inserted through a less invasive incision than required for a rigid L-shaped cannula and which avoids the difficulties of remotely guiding a flexible cannula.

SUMMARY OF THE INVENTION

This invention provides an articulating cannula for vessel occlusion, cardioplegia delivery, perfusion, aspiration, and other uses. The flexible distal end of the cannula is provided with a manipulator wire attached to an anchor. The manipulator wire extends up the rigid proximal shaft of the cannula and ends in a positionable slider or other tensioning mechanism.

By proximally positioning the slider with respect to the manipulator wire anchor, the distal end of the cannula bends into a desired angle. In one embodiment, a toroidal balloon surrounds the distal end of the cannula and is in fluid communication with a secondary lumen of the cannula. Inflation of the toroidal balloon with fluid injected through the secondary lumen occludes the vessel and prevents the cannula tip from injuring the vessel walls. A tertiary lumen which allows therapeutic fluids to be injected upstream of the artery occlusion may be proximally located with respect to the toroidal balloon. Therapeutic fluids delivered through the tertiary lumen include fluids for cardioplegia.

In an alternate embodiment, the articulating cannula can include a blood filter device disposed within the primary lumen of the cannula. In this embodiment, the blood filter device may comprise an insertion tube, an umbrella frame, an end plate, a mesh, and an adjustment device. Alternatively, the blood filter device may be disposed in a secondary lumen which opens proximally with respect to the distal end of the cannula. In this embodiment, the blood filter device may comprise a shaft, an adjustable filter frame disposed at the distal end of the shaft, a mesh, and optionally, a cantilever beam.

In yet another alternate embodiment, the articulating cannula can include a diverter associated with the distal region of the cannula. The diverter can take a number of forms, including a "windsock" embodiment. The diverter will allow the surgeon to deflect blood flow from entering other vessels during procedures such as plaque removal.

The articulation of the cannula may be summarized as follows. In operation, prior to insertion in a vessel, the surgeon may manipulate the slider distally so that the flexible distal end of the cannula is unbent. This allows the surgeon to insert the cannula at right angles to the vessel. As the distal tip of the cannula enters the vessel's lumen, the surgeon begins to proximally position the slider (tensioning mechanism) so as to bend the distal tip of the cannula. This process of inserting and bending the cannula continues until the surgeon is satisfied with the positioning of the cannula's distal end. At this point, the distal end of the cannula lies substantially parallel to the vessel within the vessel's lumen.

After positioning the distal end of the cannula in the vessel, the surgeon may then inflate the toroidal balloon in order to occlude the vessel. Alternatively, a filter mesh may be deployed within the vessel circumferentially about the distal portion of the cannula. In addition, after positioning the distal end of the cannula, the surgeon may deploy a diverter in the vessel.

In practice, this grants the surgeon the advantage of using a flexible catheter without the need to remotely guide a flexible catheter or cannula. Moreover, the surgeon does not contend with an L-shaped catheter's disadvantage of insertion maneuvering and associated incision size. The present invention allows the practitioner to use minimally invasive surgical techniques that promote faster healing and are less traumatic to the patient.

DESCRIPTION OF THE DRAWINGS

FIG. 2b is an enlarged view of the tip cover and the toroidal balloon taken along line 2b—2b of FIG. 2a.

FIG. 2c is a cross-sectional view of the slider taken along line 2c—2c of FIG. 2a.

FIG. 6b is a cross sectional view of the blood filter device taken along line 6b—6b of FIG. 6a.

DETAILED DESCRIPTION OF THE INVENTION

Figures 1A, 1B, 1C, 1D:
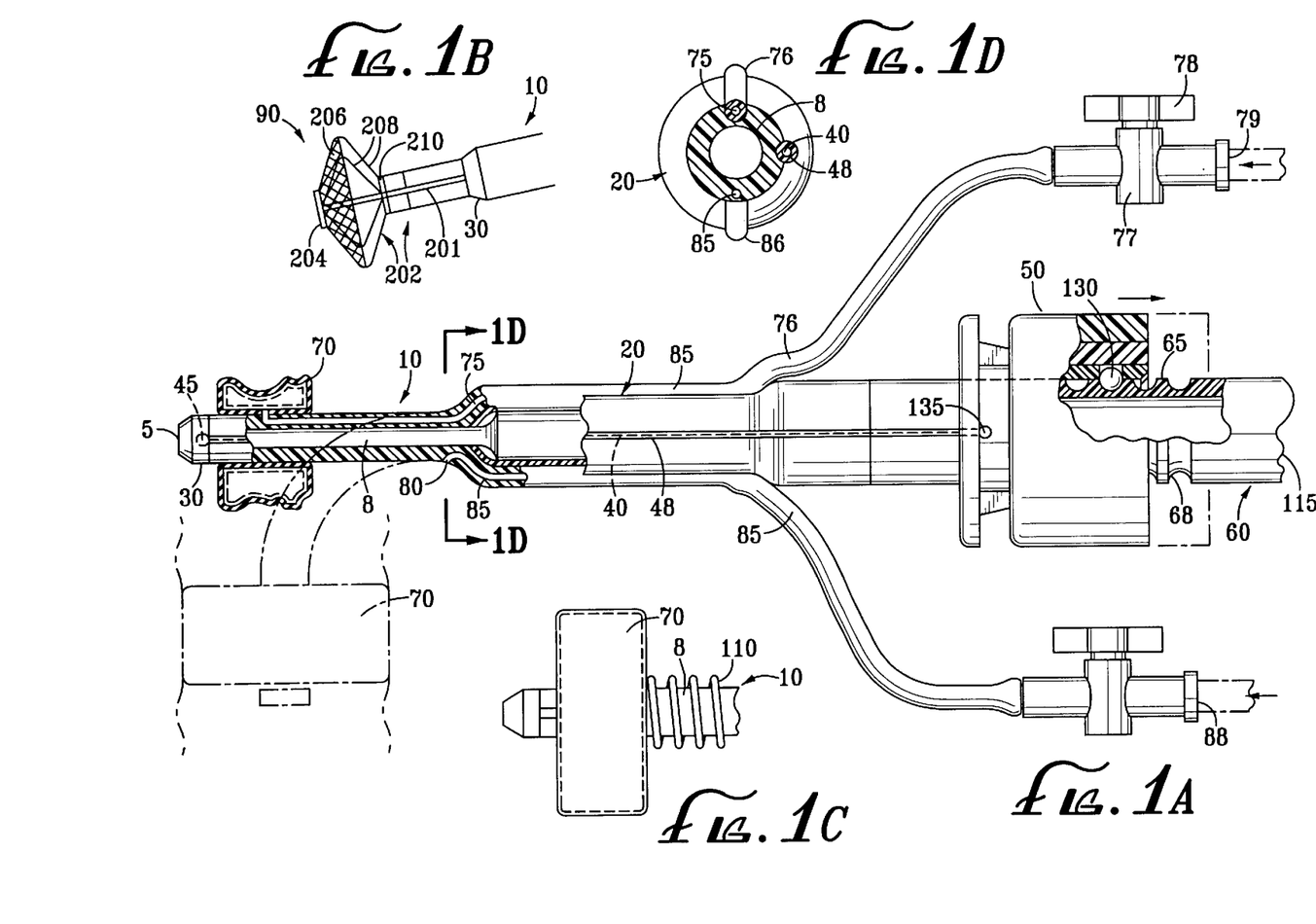
FIG. 1a is a side elevational view partially broken away of the invention with a vessel-occluding toroidal balloon circumferentially disposed about the distal region.
FIG. 1b is a perspective view of the distal region of the invention with an umbrella frame blood filter device circumferentially disposed about the distal region of the cannula.
FIG. 1c is a side elevational view of the distal region of the invention in which a coil spring surrounds the distal region of the cannula.
FIG. 1d is a cross-sectional view taken on line 1d—1d.

The present invention is directed towards an articulating cannula for use in cardiopulmonary bypass surgery and other medical procedures. One embodiment of the articulating cannula according to the present invention is shown in FIG. 1a. A flexible distal region 10 of the cannula, made of, for example, flexible polyvinyl chloride or polyethylene, is attached to a rigid proximal region 20. Proximal region may be constructed of rigid polyvinyl chloride, polyethylene, silicone, polycarbonate, or other suitable materials. Extending down both the proximal region 20 and distal region 10 is primary lumen 8 ending in primary lumen port 5. Primary lumen 8 extends proximally down the cannula and ends in input port 115 through which therapeutic fluids may be pumped. An anchor 30 is affixed about the end of the distal region 10 of the cannula. Attached to the anchor 30 is the end of a manipulator wire 40. An anchor ball 45 at the end of manipulator wire 40 secures the manipulator wire 40 to the anchor 30. Manipulator wire 40, in the embodiment shown, is disposed in a stainless steel hypodermic manipulator wire tube 48. Manipulator wire 40 is preferably constructed out of 316 L stainless steel wire. Alternatively a woven stainless steel cable or other suitable materials may be used. Manipulator wire 40 and tube 48 extend proximally from the distal region 10 of the cannula to the proximal region 20. The proximal end of manipulator wire 40 is attached to a slider 50 that, in one embodiment, is circumferentially disposed about the handle region 60 of the cannula. Slider 50 frictionally engages handle region 60 through a clamping mechanism and is positionable in a proximal and distal direction so as to bias manipulator wire 40 proximally or distally, thereby bending or straightening distal region 10. In the embodiment illustrated in FIG. 1, the slider's clamping mechanism frictionally engages teeth 65 on handle region 60 by biasing radially movable balls 130 into grooves 68 on handle region 60.

Because distal region 10 bends into a desired angle, such as a right or L-shaped angle when slider 50 is proximally displaced on handle 60, a coil spring 110, illustrated in FIG. 1c, may be integrated with the distal region 10 so as to prevent kinking of the lumen 8. Alternatively, a rigid or braid reinforced lumen could also be used to prevent kinking. In addition, coil spring 110 would provide resiliency so as to keep distal region 10 and proximal region 20 in line with one another when slider 50 is positioned distally with respect to handle 60. Use of a plurality of separated rings instead of coil spring 110 would provide an equivalent protection against kinking.

Circumferentially disposed about the distal region 10 of the cannula is a toroidal balloon 70 that is in fluid communication with a secondary lumen 75 of the cannula. Secondary lumen 75 proximally extends from toroidal balloon 70 to a proximal projection 76. Proximal projection 76 may include a valve 77 operated by stopcock 78. Fluid, such as pressurized air or water distends toroidal balloon 70 by injection into port 79 of proximal projection 76. Toroidal balloon 70 is preferably made out of a soft resilient material such as polyurethane, silicone, or latex rubber so as to expand and substantially or-completely occlude the desired vessel. Toroidal balloon's 70 size can be varied depending upon the size vessel being occluded.

Proximal to toroidal balloon 70 is a tertiary lumen port 80 connecting to tertiary lumen 85. Tertiary lumen 85 proximally extends to a tertiary proximal projection 86. Therapeutic fluids pumped down inlet 88 of tertiary proximal projection 86 provide fluids to vessel structures upstream of the toroidal balloon 70.

Tertiary proximal projection 86 may optionally be fitted with a valve and stopcock similar to those shown on the proximal projection 76.

The relationship of the various lumens is illustrated in FIG. 1d. Although the secondary lumen 75 and tertiary lumen 85 are disposed on opposite sides of the cannula in the embodiment illustrated, their exact location and their relationship to the location of manipulator wire tube 48 and manipulator wire 40 is not critical to the overall functioning of the invention.

Figure 2A:
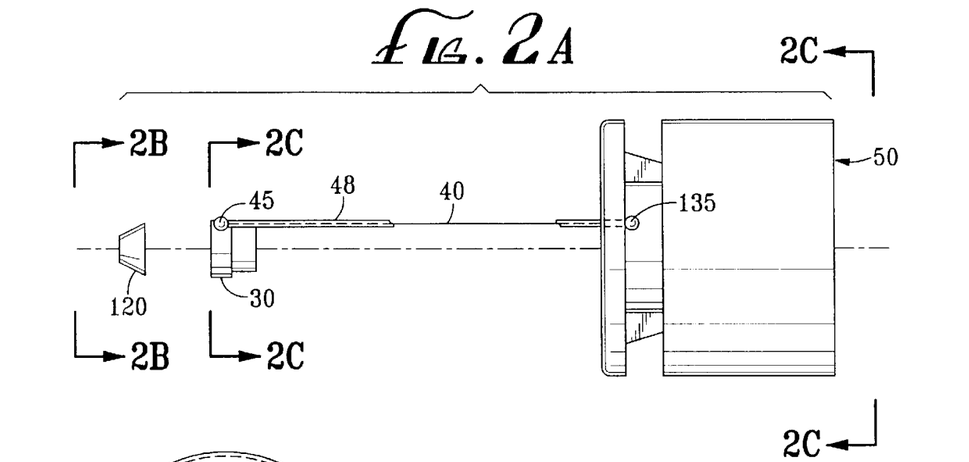
FIG. 2a is an exploded cut-away view of the anchor and the tip cover connecting to the manipulator wire, manipulator wire tube and the slider.
Figure 2B:
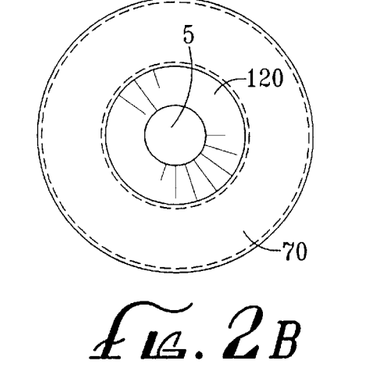
Figure 2C:
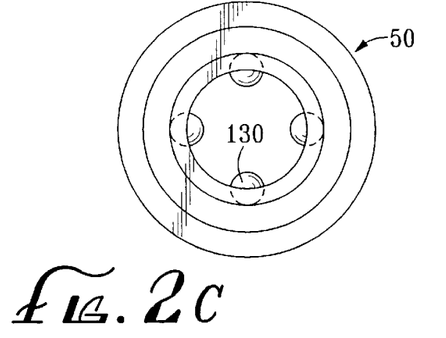

The anchor 30 may be associated with a conical tip cover 120 as illustrated in FIG. 2a. Lumen port 5 would then exit through tip cover 120 as illustrated in FIG. 2b. A pocket on anchor 30 receives anchor ball 45 of manipulator wire 40. Many other ways exist to bond manipulator wire 40 to anchor 30 such as welding, gluing and the like. In a preferred embodiment, manipulator wire 40 is disposed in a stainless steel hypodermic manipulator wire tube 48 which extends from anchor 30 to slider 50. At its proximal end, manipulator wire is attached to slider 50 with a proximal anchor ball 135. Many other suitable attachment methods exist, including welding and gluing.

Figure 3A:
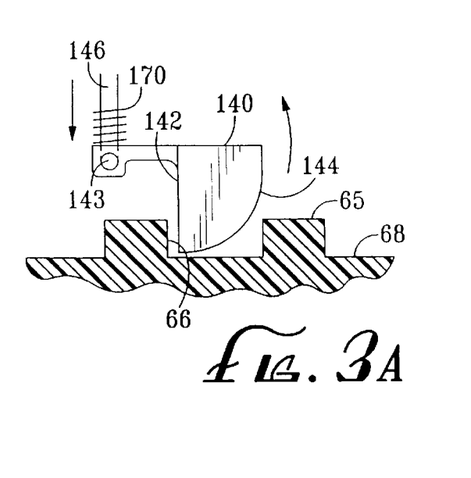
FIG. 3a is a cross-sectional view of the slider and the proximal region of the cannula wherein the slider employs a camming mechanism in order to engage the proximal region of the cannula.

The clamp or clamping mechanism by which slider 50 can be slidably positioned proximally or distally on handle 60 can be implemented in many ways. For example, as illustrated in FIG. 3a, slider 50 could be attached to cam 140. Cam 140 is biased, using a spring 170 or other suitable means, so that flat region 142 of cam 140 abuts sidewall 66 of groove 68 on handle 60. When slider 50 is moved proximally with respect to handle 60, curved surface 144 of cam 140 causes cam 140 to rotate out of groove 68 on axis 143. Because cam 140 is biased into grooves 68, as slider 50 is moved proximally to the adjacent proximal groove 68, cam 140 will rotate down into the adjacent proximal groove 68 on axis 143 so as to fix slider 50 to handle 60 in a new, proximally displaced position. This process can be repeated until slider 50 provides the desired proximal bias to manipulator wire 40, thereby bending distal region 10 of the cannula to a desired angle with respect to proximal region 20. A lever 146 rigidly attached to cam 140 at axis 143 can be used to rotate cam 140 up out of groove 68 and maintain cam 140 out of grooves 68 as the slider is distally positioned, thereby straightening distal region 10 with respect to proximal region 20.

Figure 3B:
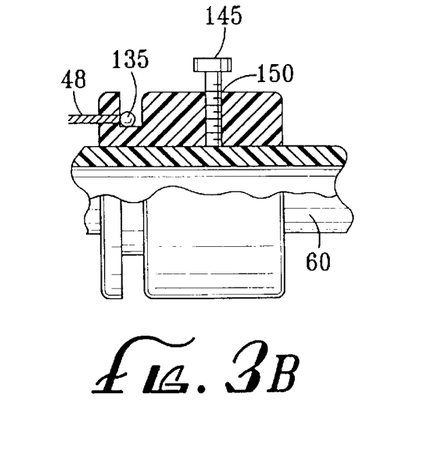
FIG. 3b is a cross-sectional view of the slider and the proximal region of the cannula wherein the slider employs a bolt or screw which passes through a threaded hole and frictionally bears against the proximal region of the cannula.

An alternative clamp or clamping mechanism for positioning slider 50 to handle 60 is illustrated in FIG. 3b. Slider 50 has a threaded hole 150 through which a bolt 145 is threaded. In this embodiment handle 60 does not require teeth 65 and grooves 68. As bolt 145 is rotated into threaded hole 150, bolt 145 frictionally bears against handle 60 and secures slider 50 in a fixed position with respect to handle 60. Those of ordinary skill in the art will realize that many other clamping mechanisms could be constructed without departing from the spirit of the present invention.

Figure 4:
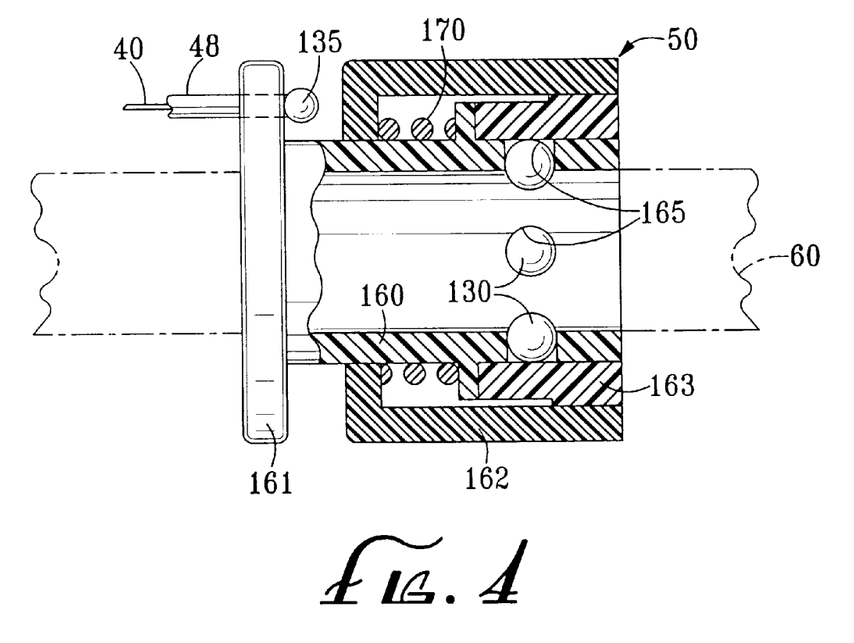
FIG. 4 illustrates a cross section of the slider according to one embodiment of the invention.

In the preferred embodiment, clamping mechanism of slider 50 is constructed according to the invention of Lee, U.S. Pat. No. 4,893,810, the contents of which are incorporated herein by reference in its entirety. The invention of Lee is commercially available as the "Grip Fast"™, manufactured by S.M.I., Inc. As illustrated in FIG. 4, this embodiment of the clamping mechanism comprises a collar body 160 with an axial flange 161. Circumferentially disposed about collar body 160 is collar sleeve 162 with a tension ring 163 having a tapered inner surface. The tapered inner surface bears against balls 130 that in turn are disposed in windows 165 on collar body 160. A spring 170 biases collar body 160 with respect to sleeve 162 so that balls 164 are forced into windows 165 by the tapered inner surface of tension ring 163. This causes balls 130 to frictionally engage teeth 65 on handle 60 (illustrated in FIG. 1), thereby clamping slider 50 to handle 60.

In order to bend the distal region 10 of the cannula, the health practitioner or surgeon grips the collar sleeve 162 of slider 50 and displaces it proximally with respect to handle 60. This proximal movement compresses spring 170 so that tension ring 163 is displaced proximally with respect to balls 130. This proximal displacement allows the balls 130 to move up out of groove 68 on handle 60 so that slider 50 can be proximally displaced with respect to handle 60.

Because manipulator wire 40 is fixed to axial flange 161 of collar body 160, manipulator wire 40 proximally displaces anchor 30, thereby bending distal region 10 of the cannula. In order to straighten this bent distal region 10 of the cannula, the surgeon follows an analogous procedure. However, rather than displace the slider 50 proximally on handle 60 of the cannula, the surgeon now displaces the slider 50 distally on handle 60 of the cannula. This distal movement releases the tension on manipulator wire 40 so that distal region 10 of the cannula straightens with respect to proximal region 20 of the cannula.

In an alternate embodiment, distal region 10 may be combined with a blood filter device 90 disposed within the primary lumen 8 of the cannula as illustrated in FIG. 1b. In this embodiment, the blood filter device may comprise an insertion tube 200, an activation tube 201, an umbrella frame 202, an end plate 204, a mesh 206, and an adjustment device 212 (illustrated in FIG. 5).

As shown in FIG. 1b, the umbrella frame 20 comprises a plurality of arms 208. The arms are sonically welded to a socket 210, which in turn is adhesive bonded to the insertion tube 200 which is dimensioned to fit within the main lumen 8 of the cannula without unnecessarily impeding blood flow. Alternatively, the socket 210 may be connected to the insertion tube 200 by welding or epoxy. The insertion tube 200 may be constructed with commercially available material such as polyvinyl, polyurethane, or other plastics. The arms 208 of the umbrella frame 202 are made of plastic or thin gauge metal. Because of the flexibility of this material, the arms 208 bend without the need for extra parts such as hinges. This simplifies assembly and reduces the chance of misassembly.

Figure 5:
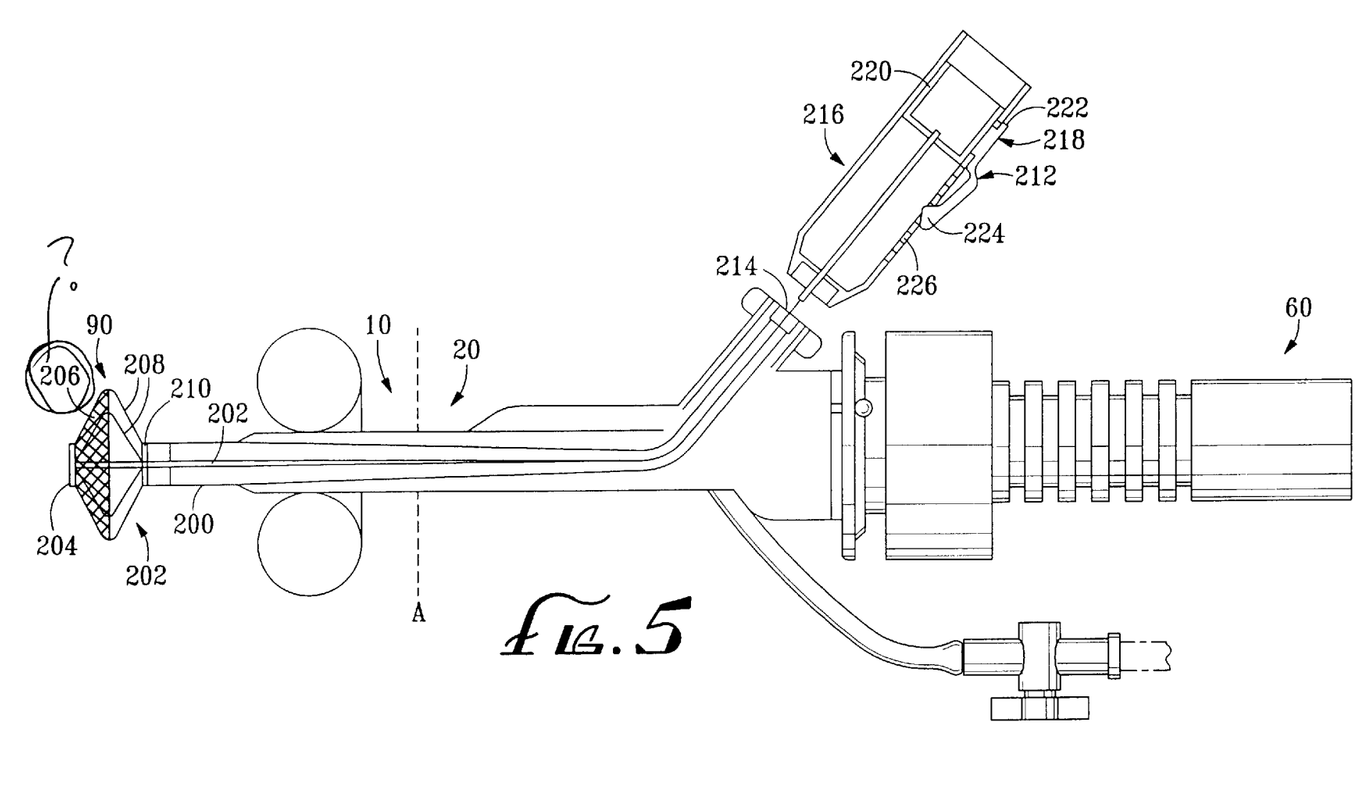
FIG. 5 is a side elevational view according to one embodiment of the invention wherein the distal end of the cannula is associated with an umbrella frame blood filter device inserted in the main lumen of the cannula.

FIG. 5 illustrates how the blood filter device 90 is actuated within the cannula. The insertion tube 200 and activation tube 201 extend proximally from socket 210 in the main lumen 8 of the cannula to the blood filter device port 214. The activation tube 201 extends from the blood filter device port 214 to the adjustment device 212 housed in blood filter device handle 216. In the embodiment illustrated, the adjustment device 212 is a linear actuation device, comprising a thumb switch 218 which is attached to a guide frame 220 which in turn is attached to the activation tube 201 via a bond joint. Thumb switch 218 comprises a base 222 and a ratchet arm 224 that moves along a ratchet slot 226, locking in predetermined intervals in a manner known in the art. Sliding the thumb switch 218 proximally from the distal region 10 of the cannula retracts the activation tube 201, which in turn draws the end plate 204 towards the socket 210. This causes the arms 208 of the umbrella frame 202 to bend and the mesh 203 to open and enable the trapping of emboli in the blood. Sliding thumb switch 218 distally pushes the activation tube 201 in the direction of the mesh 204. The activation tube 201 then pushes the end plate 204 away from socket 210, causing the arms 208 of the umbrella frame to straighten and mesh 204 to close. Further details of a blood filter device comprising an umbrella frame are described in Barbut et al, U.S. application Ser. No. 08/970,956, filed Nov. 14, 1997, the contents of which are incorporated by reference as if set forth in their entirety herein.

Figure 6A:
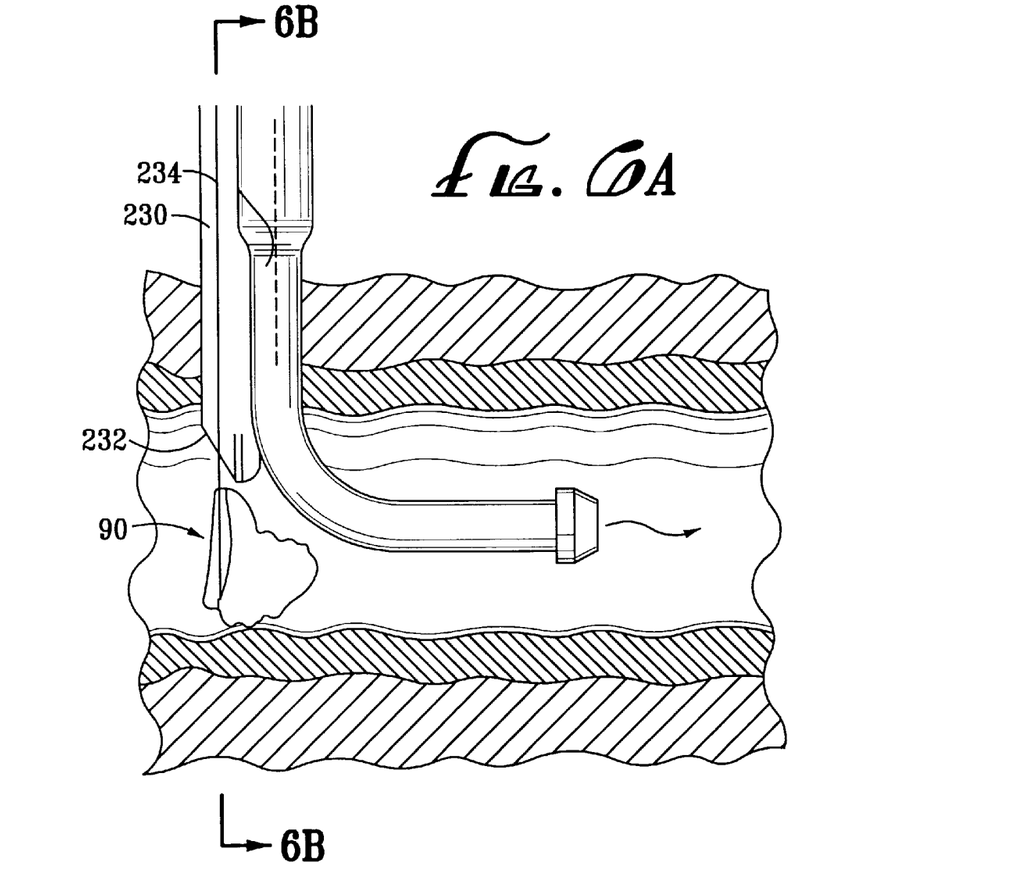
FIG. 6a is a side elevational view of the invention according to one embodiment in which the distal portion of the cannula has been inserted into a vessel and articulated and in which a filter mesh device is inserted in a secondary lumen of the cannula.

In an alternate embodiment, the blood filter device may be located proximally from primary lumen port 5 and comprise an adjustable flexible frame rather than an umbrella frame. This is illustrated in FIG. 6a, wherein the distal region 10 of the cannula has been inserted into a vessel and articulated. In this embodiment, the blood filter device 90 is inserted in a secondary lumen 230 of the cannula which ends in a secondary lumen port 232. Extending proximally from the blood filter device 90 is a flexible insertion guide 234. By distally or proximally displacing flexible insertion guide 234, blood filter device 90 can be inserted into a vessel or withdrawn from the vessel into secondary lumen 230.

Figure 6B:
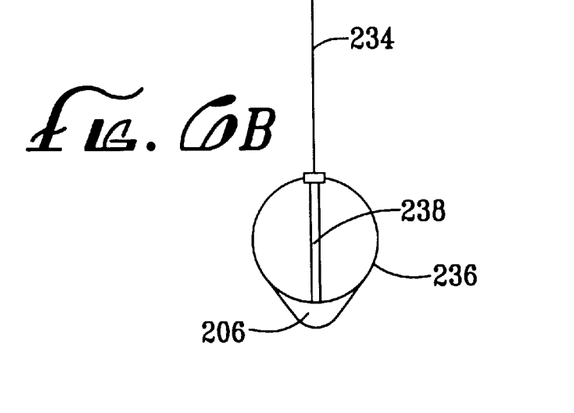
Figure 7:
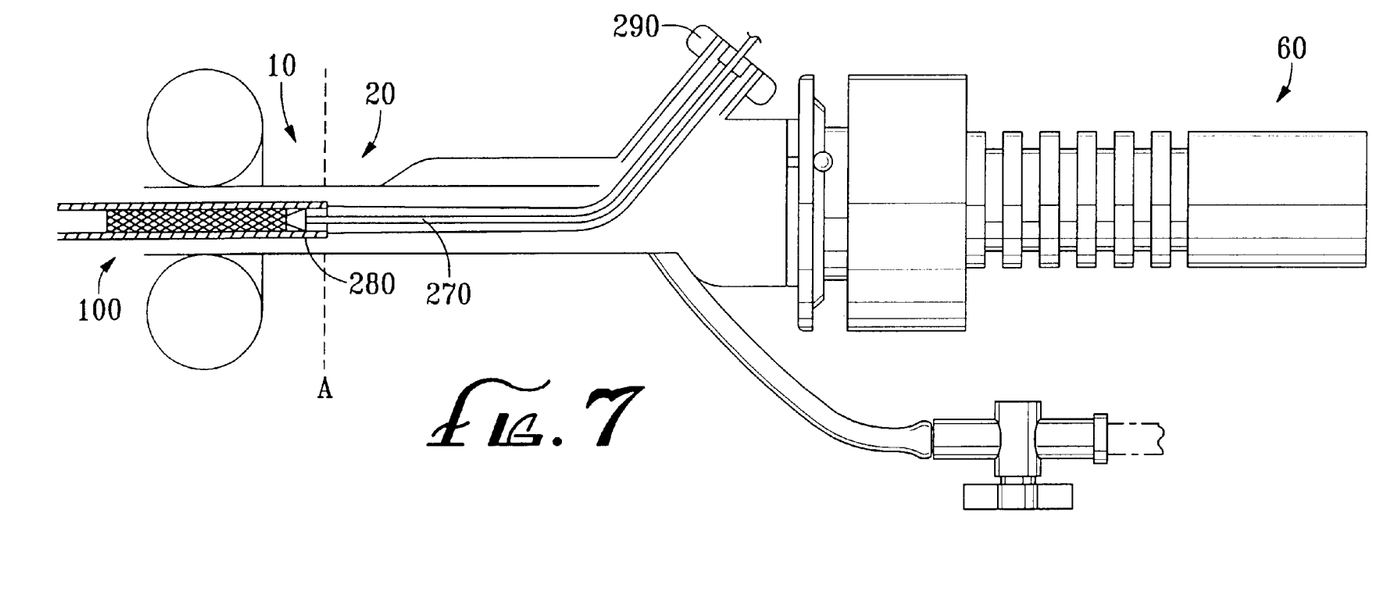
FIG. 7 is a side elevational view of the invention according to one embodiment in which the distal portion of the cannula is associated with a diverter in its compressed state.
Figure 8:
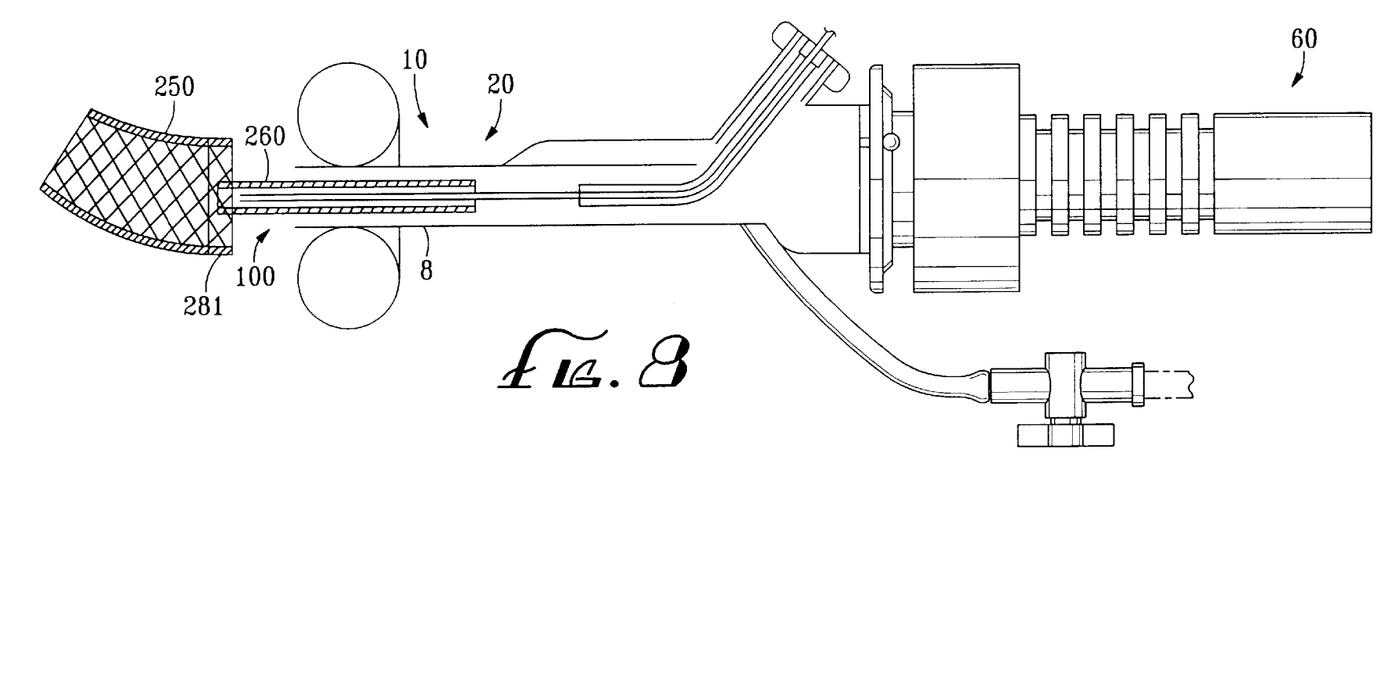
FIG. 8 is a side elevational view of the invention according to one embodiment in which the distal portion of the invention is associated with a diverter deployed in the vessel.

As illustrated in FIG. 6b, blood filter device 90 comprises a flexible frame 236, a cantilever beam 238, and a filter mesh 206. Cantilever beam 238 is attached to frame 236 at its distal end and freely slides within flexible insertion guide 234 at its proximal end. Further details of a blood filter device incorporating a flexible frame 236 and a cantilever beam 238 are described in Ambrosio, U.S. application Ser. No. 09/070,660, filed Apr. 29, 1998, the contents of which are incorporated by reference as if set forth in their entirety herein. Alternatively, distal region 10 can be combined with a diverter 100 as illustrated in FIG. 7 and FIG. 8. The use of diverter 100 allows the surgeon to prevent emboli from entering, for example, the carotid arteries during surgery. A diverter may take a number of forms, including a "snowshoe" and a "windsock" configuration. Mackenzie, U.S. application Ser. No. 08/996,532, filed Dec. 23, 1997, the contents of which are incorporated by reference in their entirety as if set forth herein, describes these diverter configurations in more detail. In the "windsock" embodiment illustrated in FIG. 7 and FIG. 8, the diverter 100 comprises a substantially cylindrical or conical wall 250 impermeable to emboli, compressibly disposed within an insertion cannula 260 which is disposed within the primary lumen 8 of the cannula. The diameter of insertion cannula 260 is sized such that fluid flow within the primary lumen 8 of the cannula is relatively unimpeded. Prior to insertion in the vessel, the clinician guides the diverter insertion cannula, which is constructed from a suitably flexible material, down a secondary projection 290 of the cannula into the main lumen 8. A piston rod 270 having a piston 280 at its distal end pushes the proximal end of the diverter to drive it out of the main lumen of the cannula into the blood vessel. The diverter is self-expanding and its proximal end is anchored within the vessel with an anchoring mechanism 281. The anchoring mechanism may comprise a sleeve adapted to frictionally engage the lumen of the vessel or any one of the following: one or more sutures, one or more clips, one or more hooks, or adhesive material.

While various embodiments of the present invention have been described above, it should be understood that they have been presented by way of example only, and not limitation. Thus, the breadth and scope of the present invention should not be limited by any of the above-described exemplary embodiments but should be defined only in accordance with the following claims and their equivalents.

What is claimed is:

1. A method of cannulating fluids to a patient, comprising the steps of:

providing an articulating cannula, the articulating cannula having a flexible distal region adapted to enter a blood vessel and a proximal region; the articulating cannula comprising:

a primary lumen extending from said distal region through said proximal region for delivery of fluids;

a slider slidably mounted on said cannula; a clamp attached to said slider, said clamp having a closed position fixing said slider to said cannula, said clamp having an open position in which said slider may be slidably displaced on said cannula; and a manipulator wire affixed to said distal region and to said slider whereby movement of said slider bends said distal region with respect to said proximal region;

inserting said cannula into a blood vessel of a patient while said slider is positioned such that said distal and proximal regions are in a relatively straight line; the cannula being inserted at an angle substantially orthogonal to the axis of the blood vessel;

applying a proximal force to said slider, whereby said manipulator wire bends said distal region with respect to said proximal region, thereby allowing the distal region to align with the axis of the blood vessel.

2. The method of claim 1, further comprising the step of inflating a balloon located about the distal region of said cannula whereby the blood vessel is substantially occluded.

3. The method of claim 1 further comprising the step of inserting an umbrella frame blood filter device through the primary lumen of said cannula into the blood vessel.

4. The method of claim 1 further comprising the step of inserting an adjustable frame blood filter device through a secondary lumen of said cannula into the blood vessel.

5. The method of claim 1 further comprising the step of inserting a diverter through the primary lumen of said cannula into the blood vessel.

* * * * *